US012733799B2

(12) United States Patent
Inoue

(10) Patent No.: US 12,733,799 B2
(45) Date of Patent: Sep. 15, 2026

(54) ENDOSCOPE

(71) Applicant: FUJIFILM Corporation, Tokyo (JP)

(72) Inventor: Masaya Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 273 days.

(21) Appl. No.: 18/466,826

(22) Filed: Sep. 14, 2023

(65) Prior Publication Data

US 2023/0414079 A1 Dec. 28, 2023

Related U.S. Application Data

(63) Continuation of application No. PCT/JP2022/004836, filed on Feb. 8, 2022.

(30) Foreign Application Priority Data

Mar. 15, 2021 (JP) ................................ 2021-041352

(51) Int. Cl.
*A61B 1/00* (2006.01)
*A61B 1/005* (2006.01)

(52) U.S. Cl.
CPC .................................. *A61B 1/0052* (2013.01)

(58) Field of Classification Search
CPC . A61B 1/0052; A61B 1/00066; A61B 1/0051; A61B 1/0042; G05G 1/01; G05G 1/08
See application file for complete search history.

(56) References Cited

U.S. PATENT DOCUMENTS 5,007,406 A 4/1991 Takahashi et al.
5,496,260 A * 3/1996 Krauter ................ A61B 1/0052 600/146
2009/0287188 A1 * 11/2009 Golden ................ A61B 1/0052 604/528
2012/0277535 A1 11/2012 Hoshino
(Continued)

FOREIGN PATENT DOCUMENTS

JP S58157433 9/1983
JP H02126825 5/1990
JP H07327913 12/1995
(Continued)

OTHER PUBLICATIONS

"International Search Report (Form PCT/ISA/210) of PCT/JP2022/004836," mailed on Apr. 26, 2022, with English translation thereof, pp. 1-5.

(Continued)

*Primary Examiner* — Anh Tuan T Nguyen
*Assistant Examiner* — Rynae E Boler
(74) *Attorney, Agent, or Firm* — JCIPRNET

(57) ABSTRACT

An endoscope includes an insertion part to be inserted into a body, and first and second angle knobs that change a direction of a distal end of the insertion part. An angle knob attaching shaft is inserted into the first and second angle knobs. An angle knob locking member is engaged with a distal end of the angle knob attaching shaft via a pressing member. When the angle knob locking member is engaged with the angle knob attaching shaft, movement of the first and second angle knobs toward a distal end side of the angle knob attaching shaft is regulated.

4 Claims, 11 Drawing Sheets

(56) References Cited

U.S. PATENT DOCUMENTS

2014/0058323 A1* 2/2014 Hoshino ............ G02B 23/2476
604/95.04
2015/0359415 A1* 12/2015 Lang ................ A61M 25/0147
600/141

FOREIGN PATENT DOCUMENTS

| | | |
|---|---|---|
| JP | H0984754 | 3/1997 |
| JP | H09294713 | 11/1997 |
| JP | 3181928 | 2/2013 |
| WO | 2012070321 | 5/2012 |

OTHER PUBLICATIONS

"Written Opinion of the International Searching Authority (Form PCT/ISA/237) of PCT/JP2022/004836," mailed on Apr. 26, 2022, with English translation thereof, pp. 1-6.

* cited by examiner

ENDOSCOPE

CROSS-REFERENCE TO RELATED APPLICATIONS

This application is a Continuation of PCT International Application No. PCT/JP2022/004836 filed on 8 Feb. 2022, which claims priority under 35 U.S.C § 119(a) to Japanese Patent Application No. 2021-041352 filed on 15 Mar. 2021. The above application is hereby expressly incorporated by reference, in its entirety, into the present application.

BACKGROUND OF THE INVENTION

1. Field of the Invention

The present invention relates to an endoscope.

2. Description of the Related Art

Endoscopes for observing the inside of a body of an observation target are widely known. The endoscope includes an insertion part to be inserted into a body of an observation target and an operation part provided to be continuously with a proximal end portion of the insertion part. The operation part is provided with an angle knob that changes a direction of a distal end of the insertion part in accordance with rotational operation, and an angle knob attaching shaft that is inserted into a rotation center of the angle knob and that pivotally supports the angle knob rotatably.

As described in JP1997-084754A (JP9-084754A) below, some endoscopes are provided with an angle knob that is attachable and detachable to an operation part. In such an endoscope, for example, the endoscope is shipped with the angle knob detached from the operation part, and the angle knob is attached to the operation part at the time of use. By providing an attachable and detachable angle knob, it is possible for a user to select from a plurality of types of angle knobs with different outer diameters and to attach and use the selected angle knob. Thus, the user can select an operation force required for bending a bendable part by selecting an angle knob to be attached. Furthermore, JP3181928U describes an attachment to be put on an angle knob. By putting the attachment on the angle knob in this manner, it is possible to reduce an operation force required for bending a bendable part.

SUMMARY OF THE INVENTION

However, conventional endoscopes have problems with easy attachment and detachment of the angle knob due to a complicated structure of the angle knob or being screwed in place.

The present invention has been made in view of the above background, and an object of the present invention is to provide an endoscope in which an angle knob is easily attached and detached.

In order to achieve the above object, there is provided an endoscope according to an aspect of the present invention including: an insertion part to be inserted into a body of an observation target; an angle knob that changes a direction of a distal end of the insertion part in accordance with rotational operation; and an angle knob attaching shaft that is inserted into a rotation center of the angle knob and that pivotally supports the angle knob rotatably, the angle knob being detached from the angle knob attaching shaft at a stage before use and being attached to the angle knob attaching shaft at the time of use, the endoscope comprising: an angle knob locking member that is attachably and detachably provided at a distal end portion of the angle knob attaching shaft and that regulates movement of the angle knob attached to the angle knob attaching shaft to a distal end side of the angle knob attaching shaft to prevent the angle knob from falling off.

There may be provided a shaft part that is provided at one of the angle knob locking member and the angle knob attaching shaft; and an opening that is provided in the other of the angle knob locking member and the angle knob attaching shaft and into which the shaft part is inserted, the shaft part having a distal end provided with a frange whose cross section perpendicular to the shaft part is formed in a non-circular shape, and the opening being formed in the same shape as the flange, in which the angle knob locking member may be attached to the angle knob attaching shaft by rotation around the shaft part after the flange penetrates the opening.

A support groove may be provided that is provided in the other of the angle knob locking member and the angle knob attaching shaft and that supports the flange having penetrated the opening in a rotatable manner around the shaft part, in which as an amount of rotation of the flange is increased from a state where the flange has penetrated the opening, a width of the support groove may be narrowed and a force required for the rotation of the flange may be increased.

There may be provided a shaft part that is provided at the angle knob locking member; and an opening that is provided in the angle knob attaching shaft and into which the shaft part is inserted, the shaft part having a distal end provided with a protrusion that protrudes toward a side of the shaft part, and the opening having an inner periphery provided with a first groove part that is formed from a distal end to a proximal end side of the angle knob attaching shaft, a second groove part that is connected to the first groove part on the proximal end side of the angle knob attaching shaft and that has an arc shape centered around the angle knob attaching shaft, and a third groove part that is connected to the second groove part on a side opposite to the first groove part and that is formed from the proximal end side to the distal end side of the angle knob attaching shaft, in which the angle knob locking member may be attached to the angle knob attaching shaft as the protrusion passes through the first groove part, the second groove part, and the third groove part in this order.

An biasing member may be provided that biases the shaft part from the proximal end side to the distal end side of the angle knob attaching shaft.

There may be provided a shaft part that is provided at the angle knob locking member; and an opening that is provided in the angle knob attaching shaft and into which the shaft part is inserted, the shaft part having a distal end provided with a spreading part that spreads toward a side of the shaft part, in which the angle knob locking member is attached to the angle knob attaching shaft as a result of spreading of the spreading part in the opening.

A releasing part may be provided at a back of the opening, the releasing part pressing the spreading part to release the spreading in a case where the angle knob locking member is further pushed into the opening.

The spreading part may be cut and fall off from the shaft part by the pressing to release the spreading.

The angle knob locking member may include a holding part that engages with the spreading part to hold the spreading part in a vicinity of the shaft part, and the spreading part may engage with the holding part via the pressing to release the spreading.

There may be provided a pressing member arranged closer to the distal end side of the angle knob attaching shaft than to the angle knob, in which the angle knob locking member may regulate movement of the angle knob toward the distal end side of the angle knob attaching shaft via the pressing member.

The pressing member may be integrated with the angle knob.

According to the present invention, it is possible to provide an endoscope in which an angle knob is easily attached and detached.

DESCRIPTION OF THE PREFERRED EMBODIMENTS

First Embodiment

Figure 1:
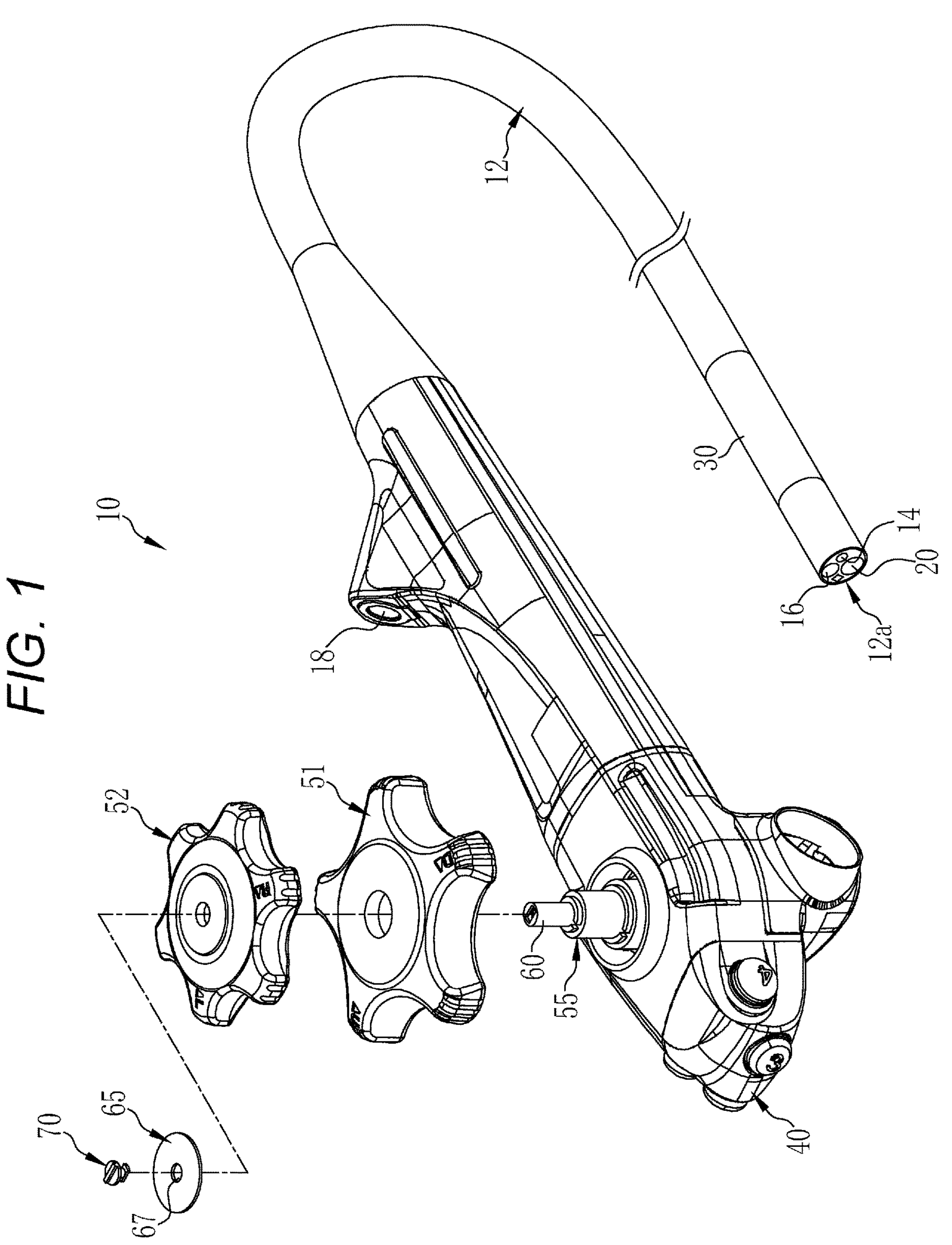
FIG. 1 is an external view of an endoscope.

In FIG. 1, an endoscope 10 includes an insertion part 12 to be inserted into a body of an observation target. At a distal end 12*a* of the insertion part 12, there are provided an illumination window 14 that emits illumination light, an observation window 16 on which light reflected from an observation target is incident, a forceps outlet 20 that is an outlet for a treatment tool such as a forceps inserted into the insertion part 12 from a forceps port 18, and the like.

A bendable part 30 is provided in the vicinity of the distal end 12*a* of the insertion part 12. The bendable part 30 is provided so as to be bended vertically and horizontally. Four wires, that is, first to fourth wires 31 to 34 (see FIG. 2), disposed inside the insertion part 12 are connected to the bendable part 30. Then, the bendable part 30 is bended in a first direction (upward in the present embodiment) by pulling the first wire 31 toward a proximal end side of the insertion part 12. In addition, by pulling the second wire 32 toward the proximal end side of the insertion part 12, the bendable part 30 is bended in a second direction (downward in the present embodiment). Furthermore, by pulling the third wire 33 toward the proximal end side of the insertion part 12, the bendable part 30 is bended in a third direction (leftward in the present embodiment). In addition, by pulling the fourth wire 34 toward the proximal end side of the insertion part 12, the bendable part 30 is bended in a fourth direction (rightward in the present embodiment).

Figure 2:
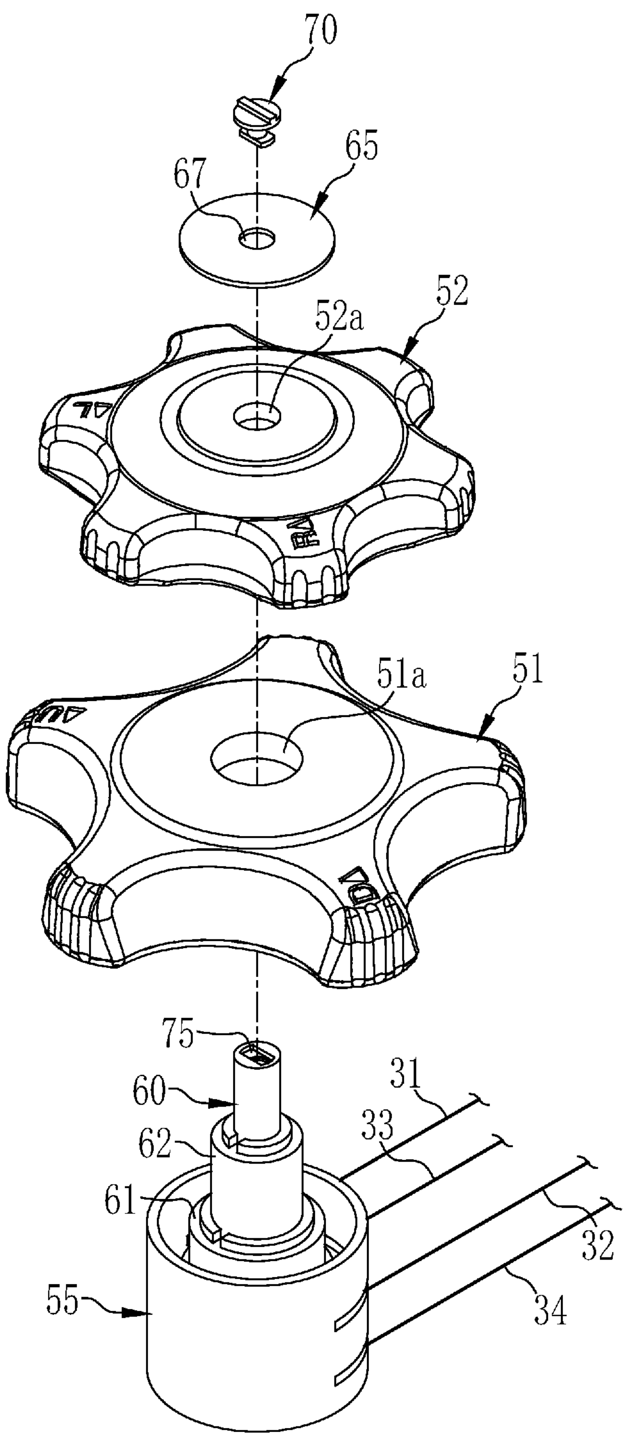
FIG. 2 is an enlarged view of an angle knob and surroundings thereof.

An operation part 40 is connected to the proximal end side of the insertion part 12. When the endoscope 10 is used, first and second angle knobs 51 and 52 are attached to the operation part 40. The operation part 40 is provided with a wire pulling mechanism 55, and as shown in FIG. 2, the wire pulling mechanism 55 is provided with an angle knob attaching shaft 60. A first insertion hole 51*a* is provided at a rotation center of the first angle knob 51, and the first angle knob 51 is pivotally supported by the angle knob attaching shaft 60 rotatably as a result of insertion of the angle knob attaching shaft 60 into the first insertion hole 51*a*. In addition, a second insertion hole 52*a* is provided at a rotation center of the second angle knob 52, and the second angle knob 52 is pivotally supported by the angle knob attaching shaft 60 rotatably as a result of insertion of the angle knob attaching shaft 60 into the second insertion hole 52*a*.

The wire pulling mechanism 55 includes a first wire pulling member 61 to which the first and second wires 31 and 32 are connected, and when the first angle knob 51 is attached to the angle knob attaching shaft 60, the first angle knob 51 is coupled to the first wire pulling member 61 to rotate integrally. Then, by rotating the first angle knob 51 in one direction (counterclockwise in the present embodiment), the first wire 31 can be pulled to direct the distal end 12*a* of the insertion part 12 upward, and by rotating the first angle knob 51 in the opposite direction (clockwise in the present embodiment), the second wire 32 can be pulled to direct the distal end 12*a* of the insertion part 12 downward.

In addition, the wire pulling mechanism 55 includes a second wire pulling member 62 to which the third and fourth wires 33 and 34 are connected, and when the second angle knob 52 is attached to the angle knob attaching shaft 60, the second angle knob 52 is coupled to the second wire pulling member 62 to rotate integrally. Then, by rotating the second angle knob 52 in one direction (counterclockwise in the present embodiment), the third wire 33 can be pulled to direct the distal end 12*a* of the insertion part 12 leftward, and by rotating the second angle knob 52 in the opposite direction (clockwise in the present embodiment), the fourth wire 34 can be pulled to direct the distal end 12*a* of the insertion part 12 rightward.

In FIGS. 1 and 2, an angle knob locking member 70 is attached to a distal end (upper end) of the angle knob attaching shaft 60 via a pressing member 65. The angle knob locking member penetrates a through hole 67 formed at the center of the pressing member 65 and is engaged with the distal end (upper end) of the angle knob attaching shaft 60 so as to be attached to the angle knob attaching shaft 60. Attaching the angle knob locking member 70 to the angle knob attaching shaft 60 in this manner regulates upward movement of the pressing member 65 arranged below the angle knob locking member 70 and the second angle knob 52 arranged below the pressing member 65. In addition, regulating upward movement of the second angle knob 52 regulates upward movement of the first angle knob 51 as well that is arranged below the second angle knob 52.

Figure 3:
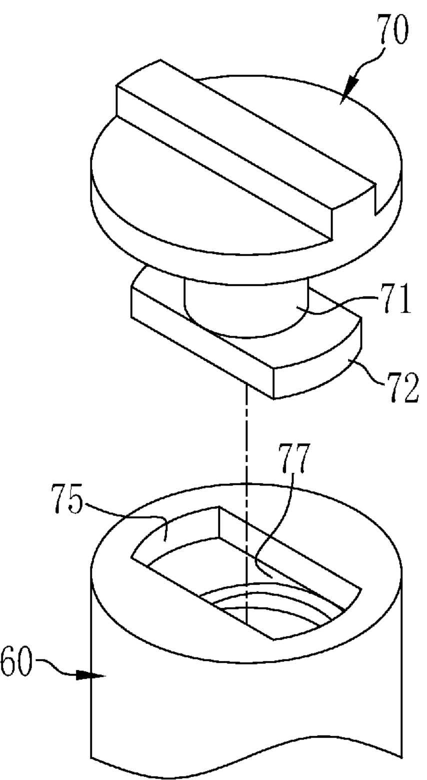
FIG. 3 is an enlarged view of an angle knob locking member and an angle knob attaching shaft.

As shown in FIG. 3, the angle knob locking member 70 has a shaft part 71 that is long in an up-down direction, and a flange 72 whose cross section perpendicular to the shaft part 71 is formed in a non-circular shape is provided at a distal end (lower end) of the shaft part 71. In addition, at the distal end (upper end) of the angle knob attaching shaft 60, an opening 75 is provided which is formed in the same shape as the flange 72 and through which the flange 72 can penetrate when the angle knob locking member 70 has a specific rotation angle (a rotation angle shown in FIG. 3) centered around the shaft part 71. With this arrangement, the angle knob locking member 70 is engaged with the opening 75 (the distal end portion of the angle knob attaching shaft 60) (the angle knob locking member 70 is attached to the angle knob attaching shaft 60) by rotating the angle knob locking member 70 around the shaft part 71 after the flange 72 is penetrated through the opening 75 with the angle knob locking member 70 set to the specific rotation angle.

As described above, in the endoscope 10, falling-off of the first and second angle knobs 51 and 52 can be easily prevented (attaching of the first and second angle knobs 51 and 52 is completed) just by rotating the angle knob locking member 70 after the flange 72 is penetrated through the opening 75. In addition, in the endoscope 10, the first and second angle knobs 51 and 52 can be easily removed just by rotating the angle knob locking member 70 to the specific rotation angle and removing the angle knob locking member 70.

Figure 4:
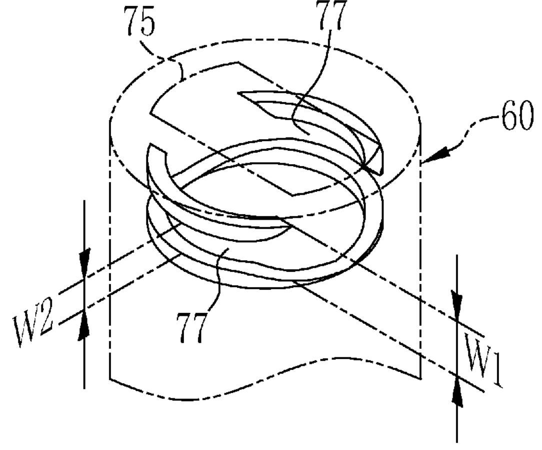
FIG. 4 is an explanatory view of a support groove.

Additionally, in the endoscope 10, as illustrated in FIG. 4, a support groove 77 that supports the flange 72 having penetrated the opening 75 is formed at the back of the opening 75 (on a proximal end side (lower side) of the angle knob attaching shaft 60). The angle knob locking member 70 (flange 72) is supported from above and below by the support groove 77 and is supported rotatably around the shaft part 71.

Then, the endoscope 10 is configured such that the support groove 77 has a width (length in an up-down direction) becoming narrower as an amount of rotation of the angle knob locking member 70 (flange 72) is increased from a state where the flange 72 has penetrated the opening (a state where the angle knob locking member 70 has the specific rotation angle described above). Specifically, the endoscope 10 is configured such that "W1>W2" is satisfied in a case where a width of the support groove 77 at a part supporting the flange 72 when the angle knob locking member 70 is at a specific rotation angle is defined as "W1" and a width of the support groove 77 at a part supporting the flange 72 when the angle knob locking member 70 is rotated degrees around the shaft part 71 from the specific rotation angle is defined as "W2". Then, the support groove 77 is formed to have the width gradually decreasing from a position of the width "W1" toward a position of the width "W2".

With this arrangement, in the endoscope 10, as the angle knob locking member 70 is rotated from the specific rotation angle, a frictional force between the flange 72 and the support groove 77 is improved, and a force required for the rotation of the angle knob locking member (flange 72) is increased. In other words, the more the angle knob locking member 70 is rotated, the more firmly the angle knob locking member 70 can be engaged with the angle knob attaching shaft 60. This contributes preventing a problem such as the angle knob locking member 70 falling off during use of the endoscope 10.

Figure 5:
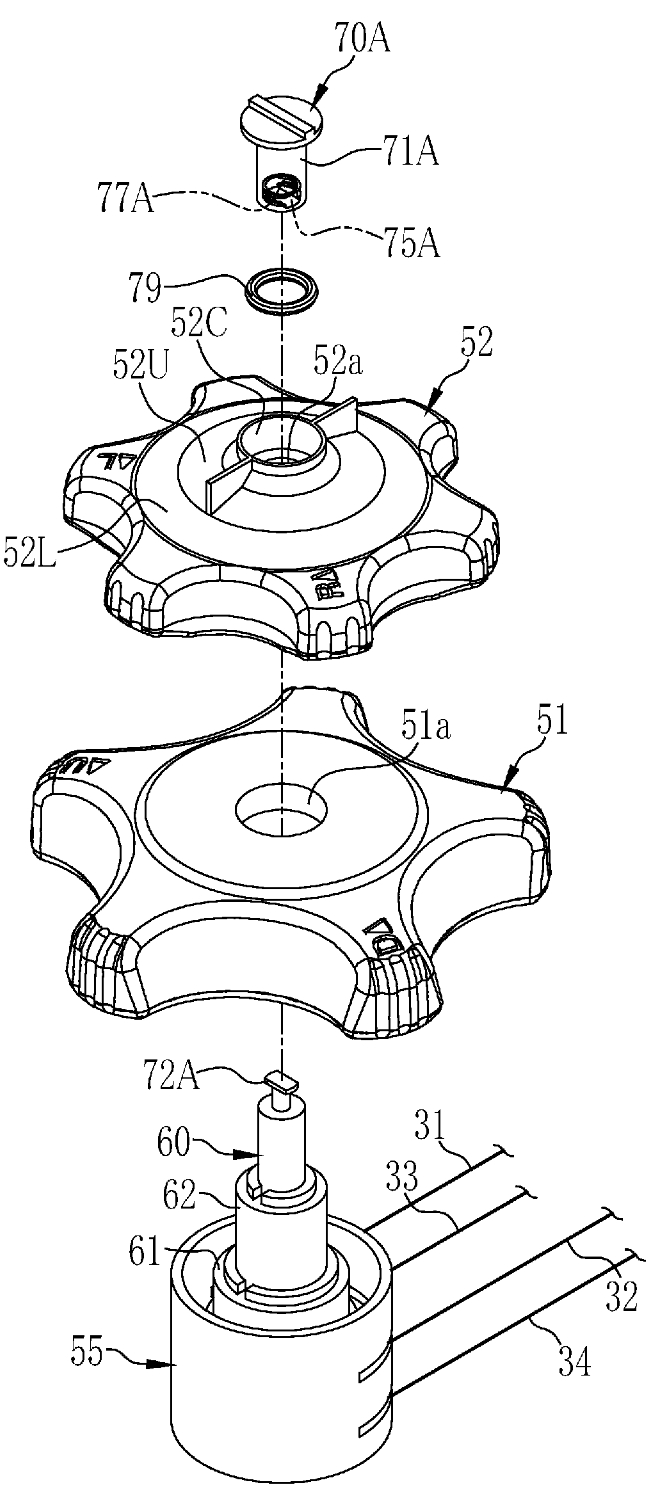
FIG. 5 is an enlarged view of the angle knob and the surroundings thereof.

Although the present embodiment has been described with respect to the example where the angle knob locking member 70 is provided with the flange 72 and the angle knob attaching shaft 60 is provided with the opening 75 through which the flange 72 penetrates, a converse configuration may be adopted as shown in FIG. 5. In description with reference to FIG. 5 and the subsequent drawings, the same members as those in the above-described embodiment will be denoted by the same reference numerals, and description thereof will be omitted.

In FIG. 5, the angle knob attaching shaft 60 is provided with a flange 72A having the same function as the flange 72 described above. In addition, an angle knob locking member has a shaft part 71A formed in a rod shape, and is provided with an opening 75A having the same function as the above-described opening 75 and being at a lower end portion of the shaft part 71A. Furthermore, the angle knob locking member 70A is provided with a support groove 77A having the same function as the above-described support groove 77 and being at the back of the opening 75A (inside the shaft part 71A).

In addition, the example of FIG. 5 is configured such that the above-described pressing member 65 (see FIG. 2) is abolished, and the angle knob locking member 70A is attached to the angle knob attaching shaft 60, thereby preventing the second angle knob 52 from falling off. Specifically, as shown in FIGS. 6 and 7, a pressing ring 52R is formed integrally with the second angle knob 52, and when the angle knob locking member 70A is attached to the angle knob attaching shaft 60, a lower end of the angle knob locking member 70A is disposed above the pressing ring 52R, whereby the second angle knob 52 is prevented from falling off (upward movement is regulated).

Furthermore, the example of FIG. 5 is configured such that when the angle knob locking member 70A is attached to the angle knob attaching shaft 60, the angle knob locking member is covered from the side. Specifically, as shown in FIGS. 6 and 7, a tubular cover 52C is provided in an upper part 52U of the second angle knob 52, whereby when the angle knob locking member 70A is attached to the angle knob attaching shaft 60, the angle knob locking member 70A is arranged in an inner peripheral portion of the cover 52C. This arrangement enables prevention of a problem such as the angle knob locking member 70A being unintentionally touched, which releases engagement between the angle knob locking member and the angle knob attaching shaft 60.

Figure 6:
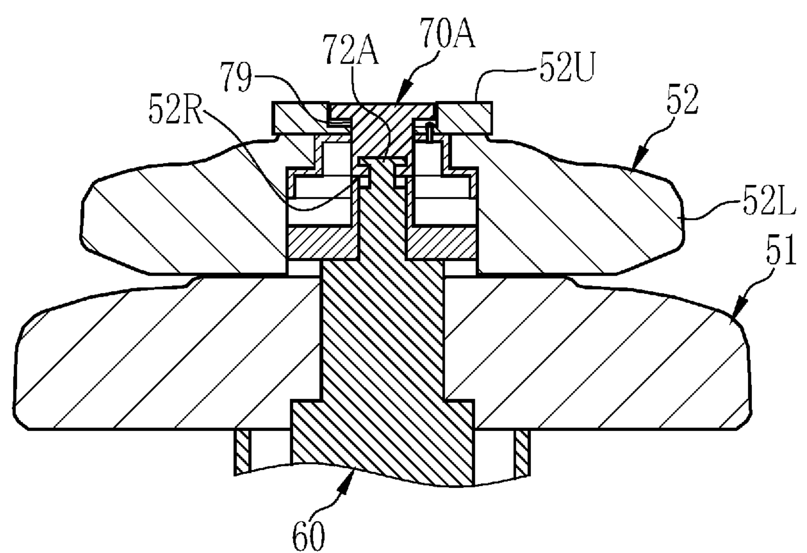
FIG. 6 is a cross-sectional view of the angle knob and the surroundings thereof.
Figure 7:
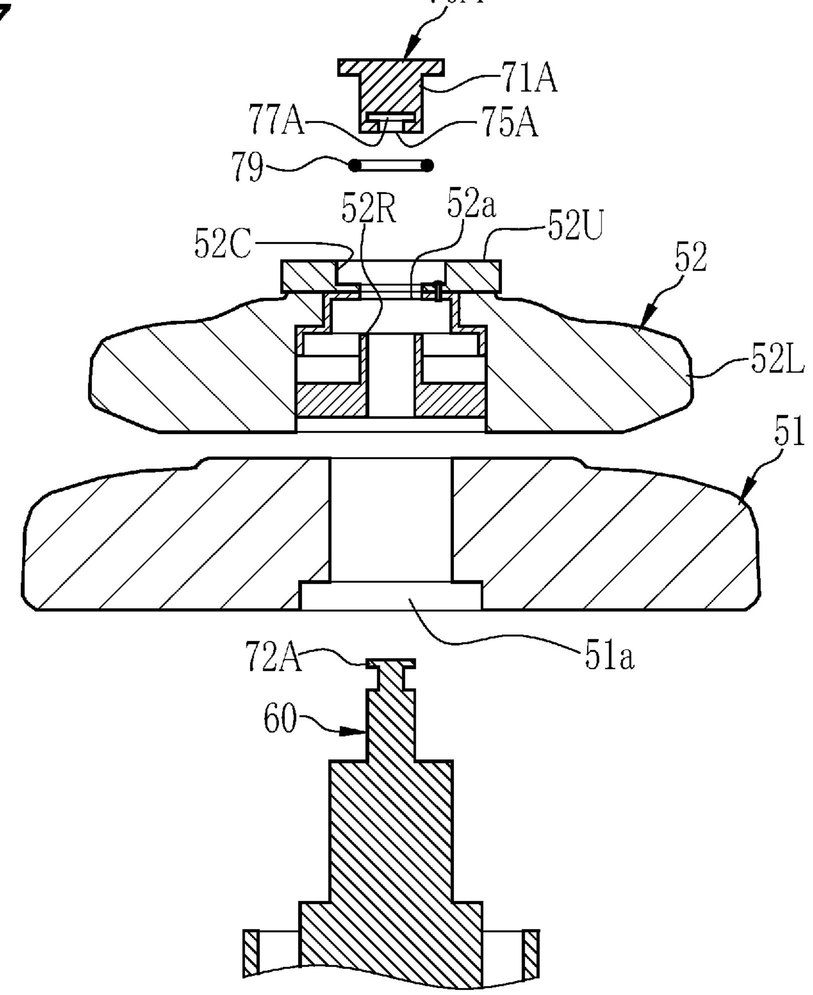
FIG. 7 is a cross-sectional view of the angle knob and the surroundings thereof.

In addition, as shown in FIGS. 5, 6, and 7, in this example, an 0 ring 79 formed of a flexible material such as a resin is provided between the angle knob locking member 70A and (the upper part 52U of) the second angle knob 52. With this arrangement, airtightness between the angle knob locking member 70A and (the upper part 52U of) the second angle knob 52 is improved. Although in this example, the upper part 52U and a lower part 52L of the angle knob locking member 70A are integrated by screwing, the upper part 52U and the lower part 52L of the angle knob locking member

70A may be formed as separate bodies, or may be integrated by a method other than screwing, for example, by bonding or integrally molding the upper part 52U and the lower part 52L.

Figure 8:
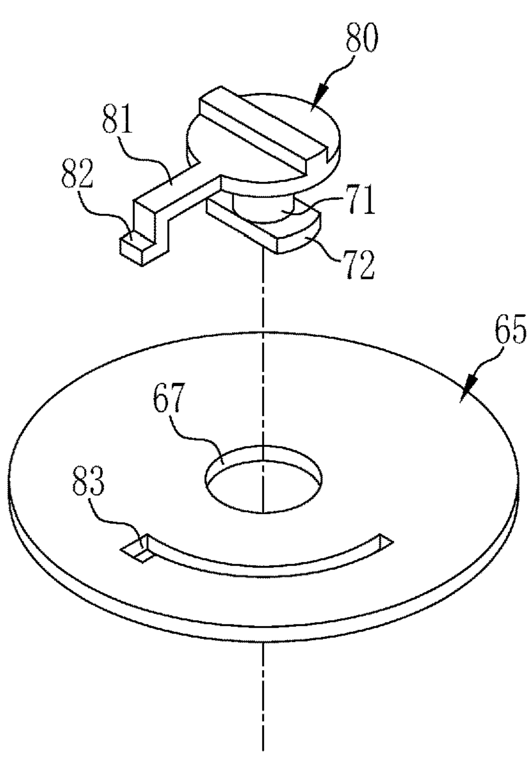
FIG. 8 is an enlarged view of the angle knob locking member and a pressing member.
Figure 9:
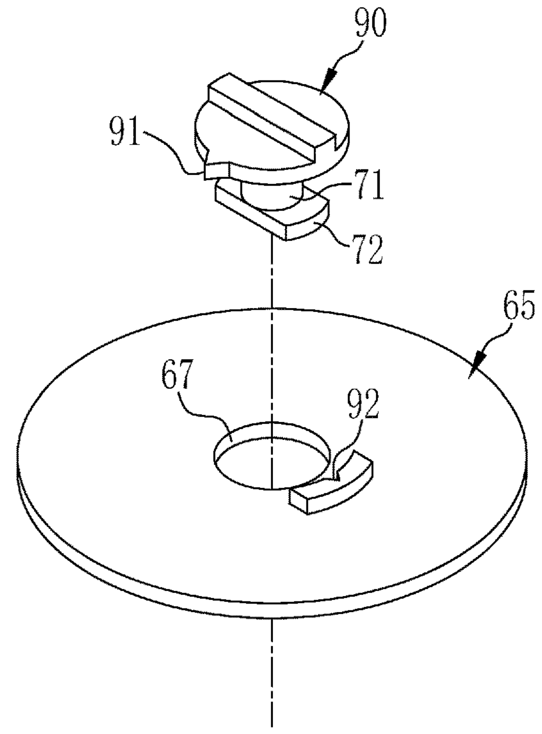
FIG. 9 is an enlarged view of the angle knob locking member and the pressing member.
Figure 10:
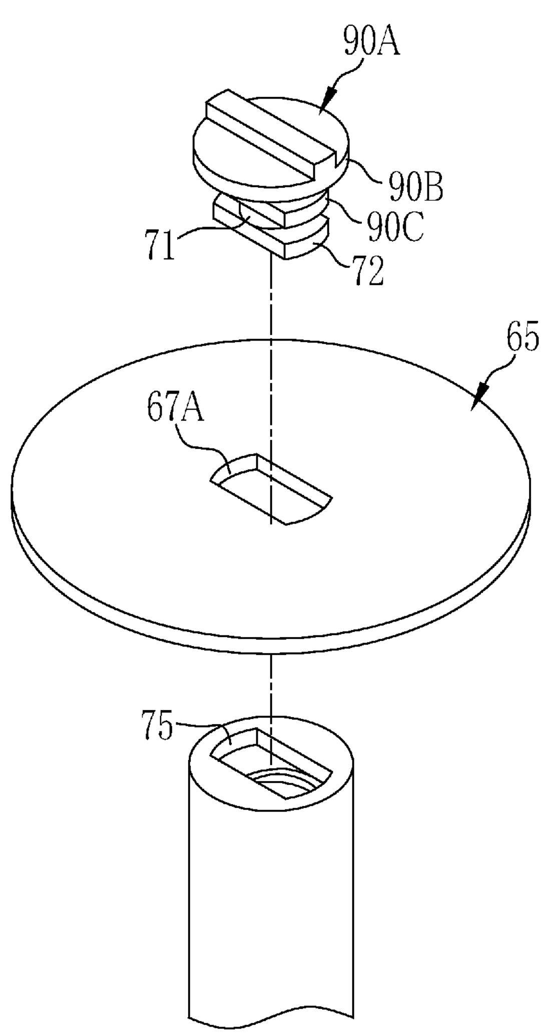
FIG. 10 is an enlarged view of the angle knob locking member and the pressing member.

In addition, although the present embodiment has been described with respect to the example in which the angle knob locking member is engaged with the angle knob attaching shaft the angle knob locking member may be engaged also with the pressing member 65 in addition to the angle knob attaching shaft 60 similarly to an angle knob locking member 80 shown in FIG. 8, an angle knob locking member 90 shown in FIG. 9, and an angle knob locking member 90A shown in FIG. 10.

Similarly to the angle knob locking member 70 described above, the angle knob locking member 80 shown in FIG. 8, the angle knob locking member 90 shown in FIG. 9, and the angle knob locking member 90A shown in FIG. 10 each have the flange 72 formed at the distal end of the shaft part 71, and are engaged with the angle knob attaching shaft 60 by causing the flange 72 to penetrate the opening 75 at a specific rotation angle and to rotate by 90 degrees around the shaft part 71.

Then, the angle knob locking member 80 shown in FIG. 8 has, at an upper portion thereof, an arm part 81 provided and extending to the side of the shaft part 71, and the arm part 81 has, at a distal end thereof, a crank-shaped engagement protrusion 82 extending to the side of the shaft part 71 after being bent downward. Meanwhile, the pressing member 65 has an engagement opening 83 formed to allow insertion and removal of the engagement protrusion 82 at a specific rotation angle, and not to allow insertion and removal of the engagement protrusion 82 when the angle knob locking member 80 is rotated from the specific rotation angle. With this arrangement, as the angle knob locking member 80 is attached to the angle knob attaching shaft 60, the engagement protrusion 82 engages with the engagement opening 83 and engages with the pressing member 65, whereby upward movement of the angle knob locking member is regulated.

Additionally, the angle knob locking member 90 illustrated in FIG. 9 has, at an upper portion thereof, an engagement protrusion 91 provided and protruding toward the side of the shaft part 71. Meanwhile, the pressing member 65 is provided with an engagement groove 92 that engages with the engagement protrusion 91 when the angle knob locking member 90 is rotated by a predetermined angle from a specific angle (in the example of FIG. 9, rotated by 90 degrees from a specific rotation angle). With this arrangement, when the angle knob locking member 90 is rotated by a predetermined angle from the specific rotation angle as the angle knob locking member 90 is attached to the angle knob attaching shaft 60, the engagement protrusion 91 engages with the engagement groove 92 and engages with the pressing member so that rotation of the angle knob locking member 90 centered around the shaft part 71 is regulated.

Furthermore, the angle knob locking member 90A illustrated in FIG. 10 is provided with a flange 90C between an upper part 90B and the flange 72. Similarly to the flange 72, the flange has a non-circular cross section perpendicular to the shaft part 71. Meanwhile, a through hole 67A is formed in the pressing member 65. Similarly to the opening 75, the through hole 67A is provided so as to allow the flange 72 and the flange 90C to penetrate the through hole when the angle knob locking member 90A has a specific rotation angle centered around the shaft part 71. With this arrangement, as the angle knob locking member 90A is attached to the angle knob attaching shaft 60, the flange 72 is engaged with the opening 75 and the flange 90C is engaged with the through hole 67A, so that the pressing member 65 is sandwiched between the upper part 90B of the angle knob locking member 90A and the flange 90C.

Although the embodiment has been described with respect to the example in which the angle knob locking member and the pressing member are separately provided, these members may be integrated by bonding, screwing, integral molding, or the like. In addition, instead of integrating the pressing member with the angle knob locking member, the pressing member may be integrated with the angle knob (the second angle knob 52 in the case of the above-described embodiment).

Second Embodiment

Figure 11:
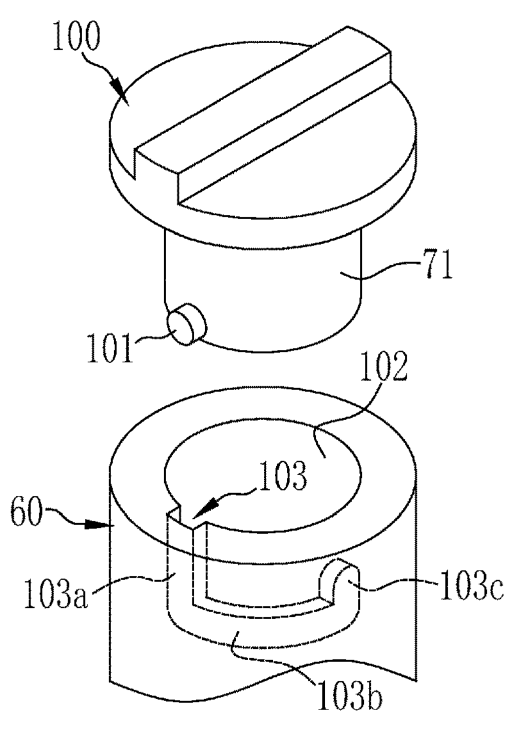
FIG. 11 is an enlarged view of the angle knob locking member and the angle knob attaching shaft.

As illustrated in FIG. 11, an angle knob locking member 100 of a second embodiment has, instead of the flange 72, a protrusion 101 that is provided at the distal end of the shaft part 71 and protrudes toward the side of the shaft part 71. In addition, in the second embodiment, a columnar opening 102 is formed at the distal end portion of the angle knob attaching shaft 60, and a groove part 103 is provided on an inner peripheral portion of the opening 102. The groove part 103 is configured with a first groove part 103*a* formed from the distal end of the angle knob attaching shaft 60 toward the proximal end side (downward), a (horizontal) arc-shaped second groove part 103*b* connected to a lower end of the first groove part 103*a* and centered around the angle knob attaching shaft 60, and a third groove part 103*c* connected to the second groove part 103*b* on the side opposite to the first groove part 103*a* and formed from the proximal end side of the angle knob attaching shaft 60 toward the distal end side (upward).

The angle knob locking member 100 is attached to the angle knob attaching shaft 60 as a result of engagement of the protrusion 101 having passed through the first groove part 103*a*, the second groove part 103*b*, and the third groove part 103*c* in this order with a terminal end portion of the groove part 103 (an upper end portion of the third groove part 103*c*). Specifically, with the protrusion 101 engaged with the first groove part 103*a*, the angle knob locking member 100 is moved downward along the first groove part 103*a*, rotated along the second groove part 103*b* and centered around the shaft part 71 by a predetermined angle (90 degrees in the example of FIG. 11), and then moved upward along the third groove part 103*c* to attach to the angle knob attaching shaft 60.

An biasing member such as a spring that biases the angle knob locking member 100 upward may be built in the angle knob attaching shaft 60, so that the angle knob locking member 100 is moved upward along the third groove part 103*c* by the biasing of the biasing member. In addition, as an angle knob locking member 110 shown in FIG. 12, the protrusion 101 may be moved upward along the third groove part 103*c* by an biasing member built in the angle knob locking member 110.

Figure 12:
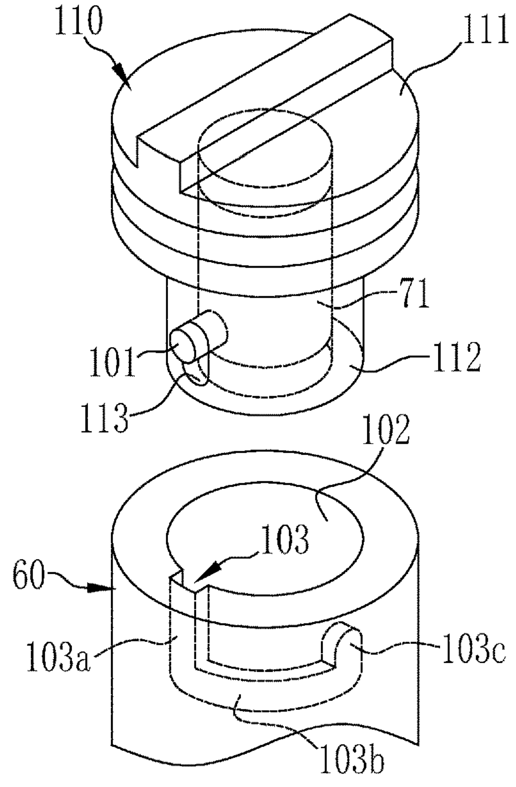
FIG. 12 is an enlarged view of the angle knob locking member and the angle knob attaching shaft.

In FIG. 12, the angle knob locking member 110 includes a main body 111 in which an upper end portion, the shaft part 71, and the protrusion 101 are integrally formed, and a tubular body 112 provided on an outer peripheral side of the main body 111. The main body 111 is supported to be vertically slidable by the tubular body 112, and the protrusion 101 protrudes from a vertically long protrusion opening 113 formed in the tubular body 112 and vertically moves along the protrusion opening 113 as the main body 111 slides.

An biasing member (not shown) that biases the main body 111 upward is built in the tubular body 112. The angle knob locking member 110 moves downward while engaging the protrusion 101 with the first groove part 103*a* and pushes the main body 111 downward of the tubular body 112, whereby the protrusion 101 can move downward and rotate along the second groove part 103*b*. When the protrusion 101 is rotated to a position of the third groove part 103*c*, the main body 111 (protrusion 101) moves upward by biasing by the biasing member and engages with the angle knob attaching shaft 60.

Although the second embodiment has been described with respect to the example in which the angle knob attaching shaft 60 is provided with the opening 102 and the groove part 103, and the angle knob locking members 100 and 110 are provided with the protrusion 101, a converse configuration may be adopted. In other words, the angle knob locking member may be provided with the opening and the groove part, and the angle knob attaching shaft may be provided with the protrusion.

Third Embodiment

Figure 13:
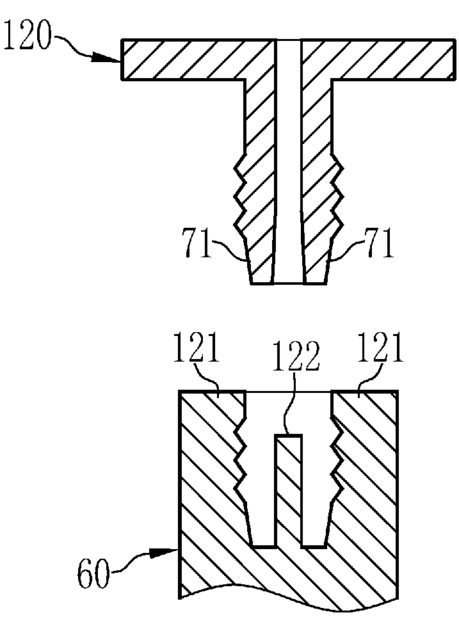
FIG. 13 is an enlarged view of the angle knob locking member and the angle knob attaching shaft.

As illustrated in FIG. 13, an angle knob locking member 120 of a third embodiment has the shaft part 71 formed in a tubular shape. Meanwhile, at the distal end (upper end) of the angle knob attaching shaft 60, an outer tube 121 that supports the shaft part 71 from an outer peripheral side thereof and an insertion pin 122 that is inserted into an inner periphery of the shaft part 71 are formed. Then, in the third embodiment, by pressing the angle knob locking member 120 downward from a state where distal ends of the angle knob locking member 120 and the angle knob attaching shaft 60 are facing each other, the shaft part 71 is sandwiched from the inside and the outside between the outer tube 121 and the insertion pin 122. As a result, the angle knob locking member 120 is engaged with the angle knob attaching shaft 60.

Although the third embodiment has been described with respect to the example in which the angle knob attaching shaft 60 is provided with the insertion pin 122, and the insertion pin 122 is inserted into the angle knob locking member 120 (shaft part 71) from below, the present invention is not limited thereto. The insertion pin 122 may be provided separately from the angle knob attaching shaft 60 and the angle knob locking member 120, and inserted into the angle knob locking member 120 from above.

Fourth Embodiment

Figure 14:
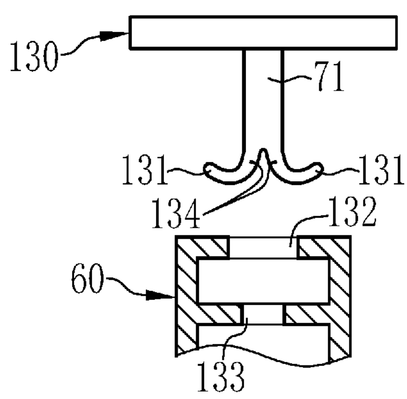
FIG. 14 is an enlarged view of the angle knob locking member and the angle knob attaching shaft.
Figure 15:
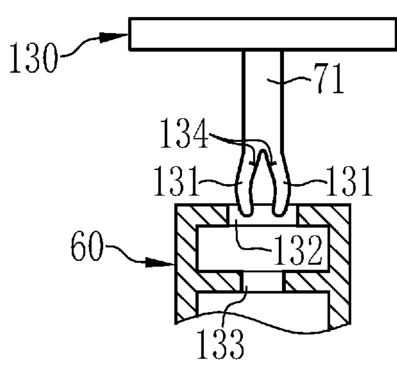
FIG. 15 is an explanatory view illustrating a state where the angle knob locking member is attached to the angle knob attaching shaft.
Figure 16:
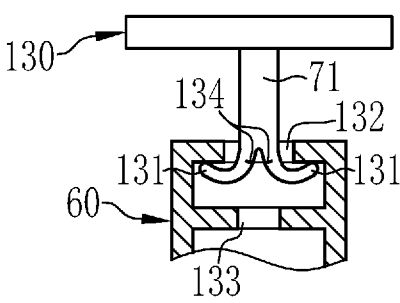
FIG. 16 is an explanatory view illustrating a state where the angle knob locking member is attached to the angle knob attaching shaft.

As illustrated in FIG. 14, an angle knob locking member 130 of a fourth embodiment has, at the distal end of the shaft part 71, a spreading part 131 that spreads toward the side of the shaft part 71. At least a part of the spreading part 131 is formed of an elastic body. Then, as illustrated in FIG. 15, the angle knob locking member 130 causes the spreading part 131 to be elastically deformed downward and to pass through an opening 132 provided at the distal end of the angle knob attaching shaft 60. As shown in FIG. 16, when passing through the opening 132, the spreading part 131 returns to a state before the elastic deformation by a force of restoration from the elastic deformation. In other words, the spreading part 131 spreads inside (back of) the opening 132. Thus, the angle knob locking member 130 and the angle knob attaching shaft 60 are engaged with each other as a result of spreading of the spreading part 131 inside the opening 132.

Figure 17:
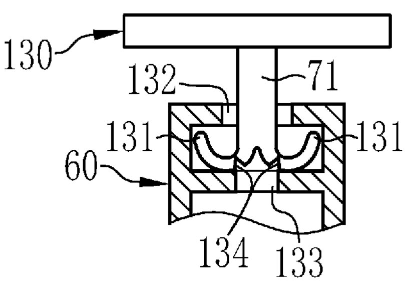
FIG. 17 is an explanatory view showing how spreading of a spreading part is released.

In addition, in the fourth embodiment, the angle knob attaching shaft 60 is provided with a releasing part 133. The releasing part 133 is configured of an opening that is provided at the back (lower side) of the opening 132 and that is slightly smaller than the opening 132. With the releasing part 133 provided in this manner, by further pushing the angle knob locking member 70 to the back side of the opening 132 from a state where the angle knob locking member 70 is engaged with the angle knob attaching shaft 60 (the state shown in FIG. 16), the spreading part 131 is pushed and bent upward by the releasing part 133, is cut, and is separated from the shaft part 71 (spreading of the spreading part 131 is released) as shown in FIG. 17. Thus, the angle knob locking member 130 can be detached from the angle knob attaching shaft 60. In the fourth embodiment, a notch 134 is provided on a lower side of a proximal end portion of the spreading part 131. By providing the notch 134 in this manner, the spreading part 131 is easily cut.

Fifth Embodiment

Figure 18:
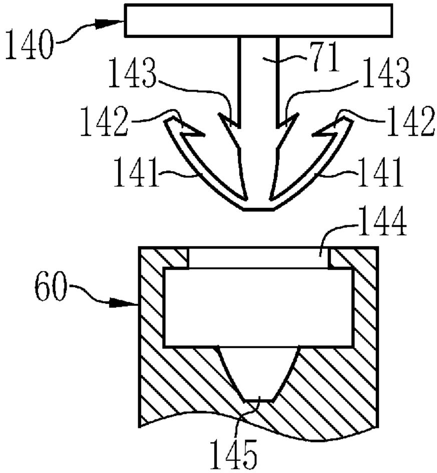
FIG. 18 is an enlarged view of the angle knob locking member and the angle knob attaching shaft.

As illustrated in FIG. 18, an angle knob locking member 140 of a fifth embodiment has, at the distal end of the shaft part 71, a spreading part 141 that spreads toward the side of the shaft part 71. At least a part of the spreading part 141 is formed of an elastic body. Then, the spreading part 141 spreads toward the side of the shaft part 71 in a state of no external force being applied (see FIGS. 18 and 20), and is elastically deformed in two stages by pressing toward the shaft part 71 (see FIGS. 19 and 21).

The first stage elastic deformation is elastic deformation (see FIG. 19) within a range in which a claw part 142 provided at a distal end of the spreading part 141 is positioned outside a holding part 143 provided at the shaft part 71. The spreading part 141 that has undergone the first stage elastic deformation returns to a state before the elastic deformation (see FIGS. 18 and 20) when the pressing toward the shaft part 71 is released. The second stage elastic deformation is elastic deformation (see FIG. 21) in which the claw part 142 gets over the holding part 143 provided at the shaft part 71 and moves to the inside of the holding part 143. The spreading part 141 that has undergone the second stage elastic deformation is held in the vicinity of the shaft part 71 as a result of engagement of the claw part 142 with the holding part 143 even after the pressing toward the shaft part 71 is released. As described above, although the spreading part 141 returns to the state of spreading from the shaft part 71 as the external force is released even when subjected to the first stage deformation, when subjected to the second stage deformation, the spreading part 141 will not return to the spreading state even when the external force is released, and is maintained in a state where spreading is released (held in the vicinity of the shaft part 71).

Figure 19:
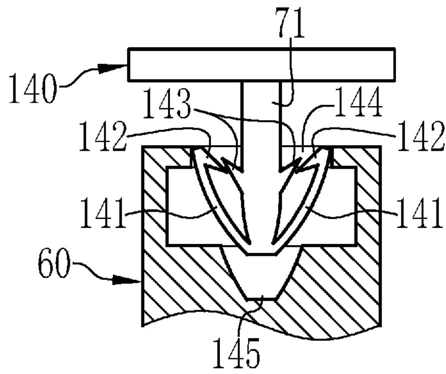
FIG. 19 is an explanatory view illustrating a state where the angle knob locking member is attached to the angle knob attaching shaft.
Figure 20:
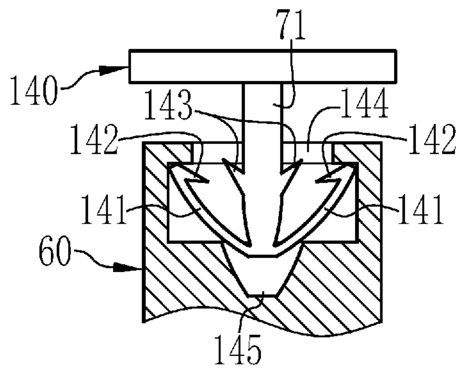
FIG. 20 is an explanatory view illustrating a state where the angle knob locking member is attached to the angle knob attaching shaft.

Then, as illustrated in FIG. 19, the angle knob locking member 140 causes the spreading part 141 to be elastically deformed up to the first stage and to pass through an opening 144 provided at the distal end of the angle knob attaching shaft 60. As illustrated in FIG. 20, when passing through the opening 144, the spreading part 141 returns to the state before the elastic deformation (the state where the spreading part 141 is spreading). In other words, the spreading part 141 spreads inside the opening 144. Thus, the angle knob locking member 140 and the angle knob attaching shaft 60 are engaged with each other as a result of spreading of the spreading part 141 inside the opening 144.

Figure 21:
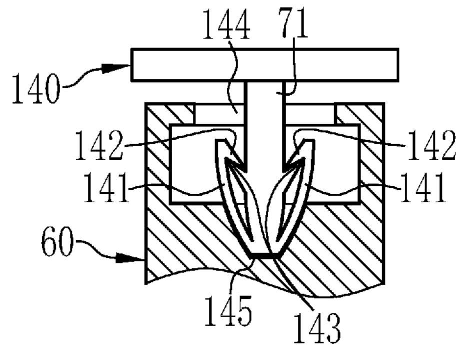
FIG. 21 is an explanatory view showing how spreading of the spreading part is released.

In addition, in the fifth embodiment, the angle knob attaching shaft 60 is provided with a releasing part 145. The releasing part 145 is a cone-shaped opening provided at the back (lower side) of the opening 144. By further pushing the angle knob locking member 140 to the back side of the opening 144 from the state where the angle knob locking member 140 is engaged with the angle knob attaching shaft 60 (the state shown in FIG. 20), the spreading part 141 is pressed toward the shaft part 71 by the releasing part 145, and the spreading part 141 is elastically deformed up to the second stage as shown in FIG. 21. Thus, the spreading part 141 is released from the spreading state and the angle knob locking member 140 can be detached from the angle knob attaching shaft 60.

Although the fourth and fifth embodiments have been described with respect to the examples in which the angle knob locking member is provided with the shaft part and the spreading part, and the angle knob attaching shaft is provided with the opening into which the shaft part is inserted and with the releasing part that releases spreading of the spreading part, a converse configuration may be adopted. In other words, the angle knob attaching shaft may be provided with the shaft part and the spreading part, and the angle knob locking member may be provided with the opening and the releasing part.

EXPLANATION OF REFERENCES

10: Endoscope
12: Insertion part
12*a*: Distal end
14: Illumination window
16: Observation window
18: Forceps port
20: Forceps outlet
30: Bendable part
31: First wire
32: Second wire
33: Third wire
34: Fourth wire
40: Operation part
51: First angle knob
51*a*: First insertion hole
52: Second angle knob
52*a*: Second insertion hole
52R: Pressing ring
52U: Upper part
52L: Lower part
52C: Cover
55: Wire pulling mechanism
60: Angle knob attaching shaft
61: First wire pulling member
62: Second wire pulling member
65: Pressing member
67, 67A: Through hole
70, 70A: Angle knob locking member
71, 71A: Shaft part
72, 72A: Flange
75, 75A: Opening
77, 77A: Support groove
79: O ring
80: Angle knob locking member
81: Arm part
82: Engagement protrusion
83: Engagement opening
90, 90A: Angle knob locking member
90B: Upper part
90C: Flange
91: Engagement protrusion
92: Engagement groove
100: Angle knob locking member
101: Protrusion
102: Opening
103: Groove part
103*a*: First groove part
103*b*: Second groove part
103*c*: Third groove part
110: Angle knob locking member
111: Main body
112: Tubular body
113: Protrusion opening
120: Angle knob locking member
121: Outer tube
122: Insertion pin
130: Angle knob locking member
131: Spreading part
132: Opening
133: Releasing part
134: Notch
140: Angle knob locking member
141: Spreading part
142: Claw part
143: Holding part
144: Opening
145: Releasing part

What is claimed is:

1. An endoscope including:

an insertion part to be inserted into a body of an observation target;

an angle knob that changes a direction of a distal end of the insertion part in accordance with rotational operation; and an angle knob attaching shaft that is inserted into a rotation center of the angle knob and that pivotally supports the angle knob rotatably, the angle knob being detached from the angle knob attaching shaft at a stage before use and being attached to the angle knob attaching shaft at the time of use, the endoscope comprising:

an angle knob locking member that is attachably and detachably provided at a distal end portion of the angle knob attaching shaft and that regulates movement of the angle knob attached to the angle knob attaching shaft to a distal end side of the angle knob attaching shaft to prevent the angle knob from falling off, wherein the endoscope further comprises:

a shaft part that is provided at one of the angle knob locking member and the angle knob attaching shaft; and an opening that is provided in the other of the angle knob locking member and the angle knob attaching shaft and into which the shaft part is inserted, an axial end of the shaft part is provided with a flange whose cross section perpendicular to the shaft part is formed in a non-circular shape, a width of the flange in the cross section perpendicular to the shaft part is greater than or equal to a diameter of the shaft part, the opening and the flange are identical in shape, and the angle knob locking member is attached to the angle knob attaching shaft by rotation around the shaft part after the flange penetrates the opening.

2. The endoscope according to claim 1, further comprising:

a support groove that is provided in the other of the angle knob locking member and the angle knob attaching shaft and that supports the flange having penetrated the opening in a rotatable manner around the shaft part, wherein as an amount of rotation of the flange is increased from a state where the flange has penetrated the opening, a width of the support groove is narrowed and a force required for the rotation of the flange is increased.

3. The endoscope according to claim 1, further comprising:

a pressing member arranged closer to the distal end side of the angle knob attaching shaft than to the angle knob, wherein the angle knob locking member regulates movement of the angle knob toward the distal end side of the angle knob attaching shaft via the pressing member.

4. The endoscope according to claim 3, wherein the pressing member is integrated with the angle knob.

* * * * *